US008753773B2

(12) United States Patent
Davis et al.

(10) Patent No.: US 8,753,773 B2
(45) Date of Patent: *Jun. 17, 2014

(54) COLORIMETRIC OR ELECTROCHEMICAL MERCURY AND TRACE METAL DETECTOR

(76) Inventors: John Perrin Davis, Bloomington, IL (US); Cheryl D. Stevenson, Bloomington, IL (US)

(*) Notice: Subject to any disclaimer, the term of this patent is extended or adjusted under 35 U.S.C. 154(b) by 137 days.

This patent is subject to a terminal disclaimer.

(21) Appl. No.: 13/507,462

(22) Filed: Jun. 29, 2012

(65) Prior Publication Data

US 2013/0001081 A1 Jan. 3, 2013

Related U.S. Application Data (60) Provisional application No. 61/571,664, filed on Jul. 1, 2011.

(51) Int. Cl.
*H01M 4/60* (2006.01)
(52) U.S. Cl.
USPC .......... 429/213; 429/212; 422/82; 422/82.01; 422/82.02
(58) Field of Classification Search
USPC .......... 422/82–82.03; 104/294; 429/212, 213, 429/218.1, 231.9, 231.95
See application file for complete search history.

(56) References Cited

U.S. PATENT DOCUMENTS

| | | | |
|---|---|---|---|
| 4,388,618 A * | 6/1983 | Finger | 340/636.15 |
| 4,497,881 A * | 2/1985 | Bertolino | 429/91 |
| 8,252,459 B2 * | 8/2012 | Stevenson et al. | 429/213 |

OTHER PUBLICATIONS

Marder et al., Third-order susceptibilities of soluble polymers derived from the ring opening metathesis copolymerization of cycloctatetraene and 1,5-cuclooctadiene, Chemistry of Materials 1989, 1, p. 171-173.*
Pop et al., State-of-the-art of battery state-of-charge determination, Measurement Science and Technology, 16, 2005, R93-R110.*
Knowlton, L. G. "Mercury and Its Compounds Their Role in Environmental Pollution." School Science and Mathematics, 1973, 73, 453-458.
Stevenson C. D.; Davis, J. P.; Reiter, R. C., "Alkoxycyclooctatetraene Anion Radicals: An Unusual Spin Density Perturbation Due to 1,3-Carbon/Carbon Interactions," J. Phys. Chem. A 1999, 103, 5343.
Soulen, R. L.; Choi, S. K.; Park, J. D. "Copper Coupling of I-Chloro-2-Iodo- and 1,2-Di-Iodo-Perfluorocycloalkenes," J. Fluorine Chem. 1973/1974, 3, 141.
Manganiello, L.; Rios, A.; Valcarcel, M. "A Method for Screening Total Mercury in Water Using a Flow Injection System with Piezoelectric Detection," Anal. Chem. 2002, 74, 921.
Fox, M. A.; Colapret, K. A. Hurst, J. R.; Soulen, R. L.; Maldonado, R. Echegoyen L. "Covalently-Linked Cyclooctatetraenyl Dianions as Sensitizers in Photoelectrochemical Cells," J. Org. Chem. 1992, 57, 3728.

(Continued)

*Primary Examiner* — Paul Hyun
*Assistant Examiner* — Robert Eom
(74) *Attorney, Agent, or Firm* — Fenningham, Stevens and Dempster LLP; David P. Fitzgibbon, Esq.

(57) ABSTRACT

A simple and low cost device to detect the presence of mercury or other trace metals in the environment and quantify said concentration by spectrophotometric, colorimetric, or electrical conductivity is disclosed. Owing to its small size, it is suitable for portable mercury detectors or detectors that may be worn as badges in the breathing zone of workers.

17 Claims, 6 Drawing Sheets

(56) References Cited

OTHER PUBLICATIONS

Stevenson, C. D.; Concepcion, J. G. "Thermodynamic Parameters for the Cyclooctatetraene Anion Radical Disproportionation as a Function of Ion Pairing in Hexamethylphosphoramide," J. Phys. Chem. 1972, 76, 2176.

Stevenson, C. D.; Concepcion, J. G.; Echegoyen, L. "The Effect of Electron Releasing Groups upon the Molecular Orbitals and Anion Disproportionation Equilibria of Substituted Cyclooctatetraenes," J. Am. Chem. Soc. 1974, 96, 5452.

Stevenson, C. D.; Concepcion, J. G. "A Study of Biscyclooctatetraene and Phenylcyclooctatetraene Anion Disproportionation Equilibria," J. Am. Chem. Soc. 1973, 95, 5692.

Stevenson, C. D.; Reiter, R. C.; Burton, R. D; Halvorsen T. D. "Electron Transfer from Rieke Cadmium Yielding Cd2+ Coordinated and Ion Associated Anion Radical Systems," Inorganic Chemistry 1995, 34, 1368.

Gerson, F.; Huber, W.; Merstetter, P.; Persy, G.; Soulen, R. L.; Spöndlin, C.; Wirz, J. "Powerful Oxidizing Properties of a Planar [8]Annulene:Tetrakis-(perfluorocyclobuta)cyclooctatetraene) and its Radical Anion," Helvetica Chimica Acta 1999, 82, 1434.

Britton, W. E.: Ferraris, J. P.; Soulen, R. L. Electrochemistry of Perfluorotetracylobuta-1,3,5,7-cyclooctatetraene, a Powerful Neutral Organic Oxidant, J. Am. Chem. Soc., 1982, 104, 5322.

Electronic Library of Construction Occupation Safety and Health, Mercury Fact Sheet, available at http://www.elcosh.org/en/document/559/d000541/mercury-fact-sheet.html utm_source=adwords&utm_medium=adwords&utm_campaign=adwords&gclid=COm01PWPwqYCFU5a7AodmzXklQ, last accessed Jun. 12, 2012.

United States Environmental Protection Agency, Controlling Power Plant Emissions: Overview, available at http://www.epa.gov/hg/control_emissions/index.htm, last accessed Jun. 12, 2012.

\* cited by examiner

1. Enclosure containing Compound 1 and solution media in a hermetically sealed container.
2. See-through window (e.g. glass, plastic) hermetically sealed for visual determination.
3. Hermetically sealed selective membrane (such as gold foil) window.
4. Electrode (1 of 2) for conductivity measurements extending into container media.
5. Hermetic seal for electrode (1 of 2).
6. Electrode (2 of 2) for conductivity measurements extending into container media.
7. Hermetic seal for electrode (2 of 2).
8. See-through window (e.g. glass, plastic, quartz) hermetically sealed for spectrophotometric determination (1 of 2).
9. See-through window (e.g. glass, plastic, quartz) hermetically sealed for spectrophotometric determination (2 of 2).

Figure 4

1. Selective membrane
2. Colored Indicator light (LED) shows ON, flashes when battery low
3. Colored Detection Indicator (LED) lights when trace metal is detected at threshold level
4. Window for visible color change (optional)
5. Audible alarm (piezoelectric) sounds at threshold(s), intermittent or continuous alarm settings
6. Out-put PORT for download of data
7. Monitor digital display readout (LCD or other)
8. Buttons (three)
9. See Inset, below, Figure 6
10. Battery recharge port
11. Battery compartment
12. Vibrator unit (optional)
13. Built-in air pump (optional)
14. Built-in air pump out-let
15. Built-in air pump inlet (small hose connects to active region-not shown)

Figure 5

INSET (side view)

1. Optional air inlet valve (closed in "passive mode", open in active "pump mode")
2. Air semi-permeable membrane ("passive mode") or platic cover ("pump mode")
3. Selective membrane (e.g. gold foil)
4. Electrode (1 of 2) measures conductivity of active region
5. Active region containing Compound 1 or similar (may be in solution)
6. Current collector electrode (2 of 2) completes circuit for first electrode
7. Transparent window (1 of 2) Light Inlet for optical density dtermination
8. Transparent window (2 of 2) Light Outlet (lined up with 7.) for optical density dtermination
9. Optional valve to air-pump hose (closed in "passive mode", open in active "pump mode")
10. Hermetically sealed relatively inert containment (e.g. glass, teflon, plastic, or ceramic)

Figure 6

COLORIMETRIC OR ELECTROCHEMICAL MERCURY AND TRACE METAL DETECTOR

CROSS-REFERENCE

A Provisional Patent Application covering the below described invention was submitted, via Express Mail, which bore label number EG 835094481 US, and was assigned application No. 61/571,664. The inventors claim the priority date of said Provisional Patent Application.

GOVERNMENT RIGHTS

Not Applicable.

BACKGROUND

Mercury is a deleterious anthropogenic pollutant. Mercury is a heavy, silvery, odorless liquid that may be released into the atmosphere in a number of ways, including but not limited to, the burning of fossil fuels. In 1999, the Environmental Protection Agency ("EPA") estimated that a year's worth of coal (in the US) contains approximately 75 tons of mercury, and the burning of this coal will lead to about 50 tons of mercury being released into our atmosphere. As part of this release mercury settles in the aquatic biosphere rendering fish potentially poisonous with recommended exposure limits. Additionally, mercury has been incorporated into everyday items, such as long-tube fluorescent light bulbs, which contain on average from 10 to 20 mg of mercury that affects the environment if not disposed of properly.

Adding to mercury's toxicity is the fact that at normal temperatures, mercury can evaporate into the air. Furthermore, when it is heated, this evaporation occurs at an elevated rate. Mercury vapor is extremely toxic to inhale, but difficult to detect due to its colorless and odorless nature. An acute exposure to mercury vapor inhaled into the lung results in a variety of lung and neurological problems including: headaches, cough, chest pain, and difficulty breathing. Continued exposure will eventually lead to loss of teeth, nausea, diarrhea and permanent lung scarring. Further, this exposure can cause severe kidney damage. Long-term exposure to mercury may cause shaking of the hands and facial muscles. However, the most deleterious neurological effects may be: headaches, trouble sleeping, personality change, memory loss, irritability, indecisiveness and loss of intelligence. Many of these symptoms can be attenuated or eliminated by avoiding further exposure, but first personnel must be able to detect mercury vapor in such areas. The termination of exposure is cogent because continual chronic exposure results in permanent injury. Consequently, mercury vapor is of major concern in the work environment, yet real-time detection and measurement of ambient mercury vapor remains costly and limited to bulky devices unsuitable to be worn in the breathing zone of workers.

In part, as a result of this heightened understanding of the consequences to humans and the environment posed by mercury and the costs associated with reducing and monitoring the release of mercury, in 1990 the Clean Air Act was amended, and the EPA was given authority to regulate mercury emissions. In recent years, the EPA has reduced the permitted concentration levels of mercury to trace levels (e.g. pursuant to the EPA the permitted concentration of mercury in drinking water is 0.002 part per million) to protect against these adverse health effects. Due to the EPA's regulations there is a need to measure the concentrations of various metal species, and this need is exacerbated by the lack of technologies to measure the presence of metals in the ultra-low (trace) concentration range. Currently only Atomic Absorbance, Atomic Emission, and Atomic Fluorescence Spectroscopies and their variants, and gold electrode conductivity meters are suitable for measurement, but such techniques require expensive and bulky equipment unsuitable for direct read operation in the breathing zone. For these reasons there is a need for a portable and comparatively inexpensive instrument, which allows for multiple approaches to detection and quantification of trace elements.

SUMMARY

The above listed applicants identified a portable and comparatively inexpensive instrument, which allows for multiple approaches to detection and quantification of trace elements, which incorporates a cavity cell separated from the environment via a selectively permeable membrane. The cavity contains a specifically designed compound comprising an electron accepting reagent comprising at least one cyclooctatetraene ("COT") moiety which forms a complex with the mercury or other trace metal. As trace metals pass through the selectively permeable membrane, they are exposed to the electron accepting reagent. A charge transfer complex is formed when the energetics of electron transfer are favorable between the trace metal and the cyclooctatetraene moiety, which can be made more favorable (and selective) by inclusion of a solution media in said cavity. By way of example, said solution may contain toluene, glyme, acetonitrile, dimethylformamide, hexamethyiphosphoramide, tetrahydrofuran, or other aprotic polar solvent in addition to the cyclooctatetraene moiety containing component. The exposure of the trace elements to the electron accepting reagent results in a quantifiably measurable change. By way of example, such a quantifiably measurable change may be a color change, change in optical density at a given wavelength, or a change in conductivity. Furthermore, the resulting change may be quantitatively measured via optical or electrical measurements.

DRAWINGS

These and other features, aspects and advantages of the present invention will become better understood with reference to the following description, appended claims and accompanying drawings where:

DESCRIPTION

The invention involves a cavity cell separated from the environment via a selectively permeable membrane. By way of example, the selectively permeable membrane may be comprised of gold foil (for trace mercury detection), polymers or block co-polymers comprised of polyethylene, polyfluorinated polymers, and/or polypropylene polymers. Said membranes may be embedded with chelating agents. By way of example, said chelating agents may be comprised of crown ethers, aza-crown ethers, cyclen, cryptands, and/or secondary or tertiary amines. The cavity contains a specifically designed compound that is an electron accepting reagent where the compound contains at least one cyclooctatetraene ("COT") moiety. The cavity may contain said specifically designed compound in solution. Said solution may be comprised of toluene, glyme, acetonitrile, dimethylformamide, hexamethylphosphoramide, tetrahydrofuran, or other aprotic polar solvent. Said solution may also contain chelating agents comprised of crown ethers, aza-crown ethers, cyclen, cryptands, or amines.

This invention may be utilized to determine the ambient concentration of mercury. Since mercury is absorbed by gold to form the well known Au—Hg amalgam, some of the ambient mercury will be drawn into the cell and affect a dramatic color change in the solution containing said electron accepting reagent. The use of gold foil as the selectively permeable membrane would be preferable for a mercury detection system, as mercury is capable of passing through the gold foil. However, for the identification of alternate trace metals, it will be understood that the use of alternate selectively permeable membranes in conjunction with alternate electron accepting reagents may enable the device to quantify elements other than mercury.

The invention may be adapted for mercury or other trace metal detection direct read dosimetry badges or portable trace metal detectors. The utilization of the electron accepting reagent or analogues thereof, described below, renders the chemistry unique to the intended purpose of detecting trace metals, such as mercury.

Herein, the electron accepting reagent is comprised of at least one COT moiety which may be described as an eight carbon mono-cyclic ring wherein all eight carbons are covalently linked to two adjacent carbons forming the eight member ring and where each of the eight cyclic ring carbons will additionally have one covalent bond to one other atom apiece. Said one other atom may be a carbon, hydrogen, or a halogen. It is preferred that said one other atom be part of a subunit which is both electron withdrawing and contributes increased planarity to the parent cyclooctatetraene moiety. Such systems have the most favorable energetics for forming the charge transfer complex. By way of example, tetrakis (tetrafluorocyclobutyl) annulated cycloctatetraenes (e.g. Compound 1 depicted below) is preferred for trace mercury detection.

The simplest form of COT used as an electron accepting reagent is represented by a single molecule of COT, or an assembly of COT moieties connected to each other directly via covalent linkages, or by a shared covalently bonded substituent, or where the COT moieties themselves share carbons. Additionally, the COT moieties may be substituted, including annulations. Below are some examples of "simple COT molecules" wherein the molecule contains only one COT moiety per unit molecule. Here, $R_1$, $R_2$, $R_3$, $R_4$, $R_5$, $R_6$, $R_7$, and $R_8$ may be taken to represent substituents outlined above.

Simple COT

Simple COT

The COT moiety may also be annulated by at least one additional cyclic ring(s). Herein, molecules containing annulated COT moieties may be described as comprising at least one COT moiety, where each of the eight cyclic ring carbons will additionally have one covalent bond to exactly one other atom apiece, wherein at least two ring carbon atoms are shared between a COT moiety and additional cyclic ring(s). Said additional cyclic ring(s) may be comprised of a 3-, 4-, 5-, 6-, 7-, or 8-membered cyclic ring(s) comprised of carbon, oxygen, nitrogen, phosphorus, sulfur, silicon, and/or boron atoms. Such molecules may be referred to as "annulated COT molecules." In such annulated COT molecules said carbon atoms of the COT moiety are either shared by said additional cyclic ring(s) or have one covalent bond to exactly one other atom apiece, where said one other atom may be a carbon, hydrogen, or a halogen.

Below are some examples of annulated COT molecules. Here, $R_1$, $R_2$, $R_3$, $R_4$, $R_5$, $R_6$, $R_7$, $R_8$, $R_9$, and $R_{10}$ may be taken to represent substituents outlined above.

a cyclobutcyclooctatetraene
(a cyclobut-[8]annulene)

A COT molecule comprised of tetrakis(perfluorocyclobuta) cyclooctatetraene ("Compound 1") below, or analogues thereof are preferred electron accepting reagents for the detection of trace metals, as Compound 1 has been found to be effective in extracting electron(s) from trace metals and thereby forming anion radicals and dianions.

Compound 1

Examples of Analogues of Compound 1

The electron accepting system may include one or more of such analogous mono, di, tri, and non-annulated compounds, [5]-annulated, [3]-annulated and all fluorinated to various degrees and in various proportions or mixtures thereof.

The COT moiety, or any molecule containing at least one COT moiety, may also be incorporated into a polymer structure. For example, see structures below.

R = a molecule containing at least one COT moiety

Example of pendent-type polymer, where COT is the Pendant Group on a polymer backbone Example of Pendant-type polymer, where Compound 1 is the Pendant Group on a polymer backbone Several modes of viable detection have been identified (e.g. conductivity, resistivity, potentiometric, spectrophotometric, and colorimetric), but those involving optical density and conductivity are easiest to construct and provide the best method of detection.

Figure 1:
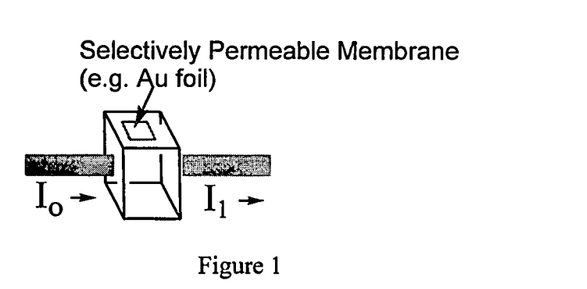
FIG. 1 shows a version of the detector cavity where the Beer-Lambert Law is used to spectrophotometrically determine the concentration of trace metal.
Figure 2:
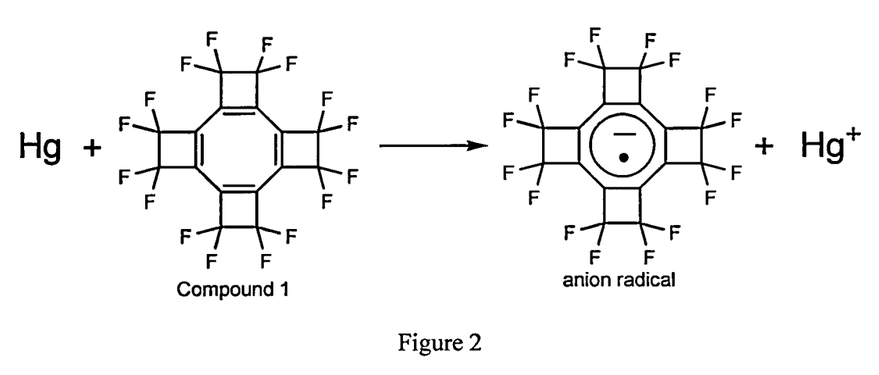
FIG. 2 shows a version of the trace metal charge transfer complex formed where the trace metal is mercury and the cyclooctatetraene containing component is Compound 1.
Figure 3:
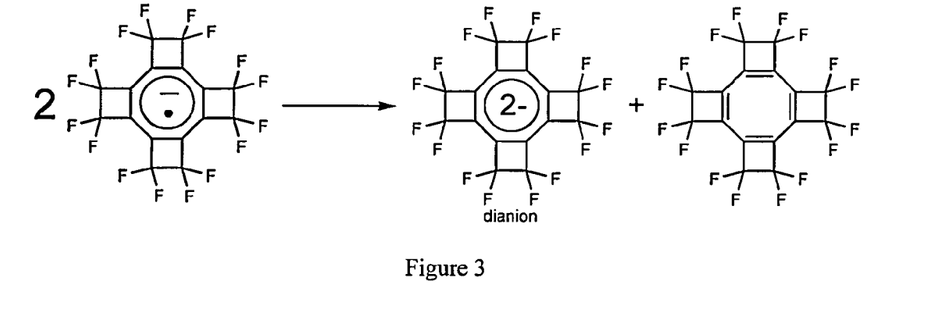
FIG. 3 shows a version of the disproportionation reaction that occurs for the radical anion of the cyclooctatetraene component of the charge transfer complex (here, Compound 1 is shown)
Figure 4:
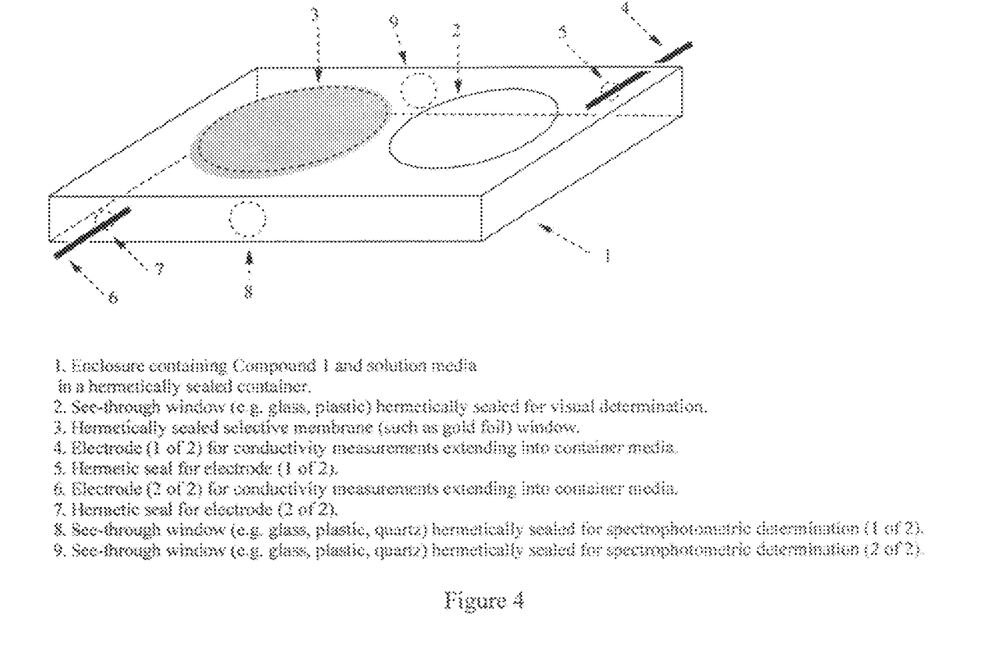
FIG. 4 shows a version of the main features of the cavity portion of the detector.
Figure 5:
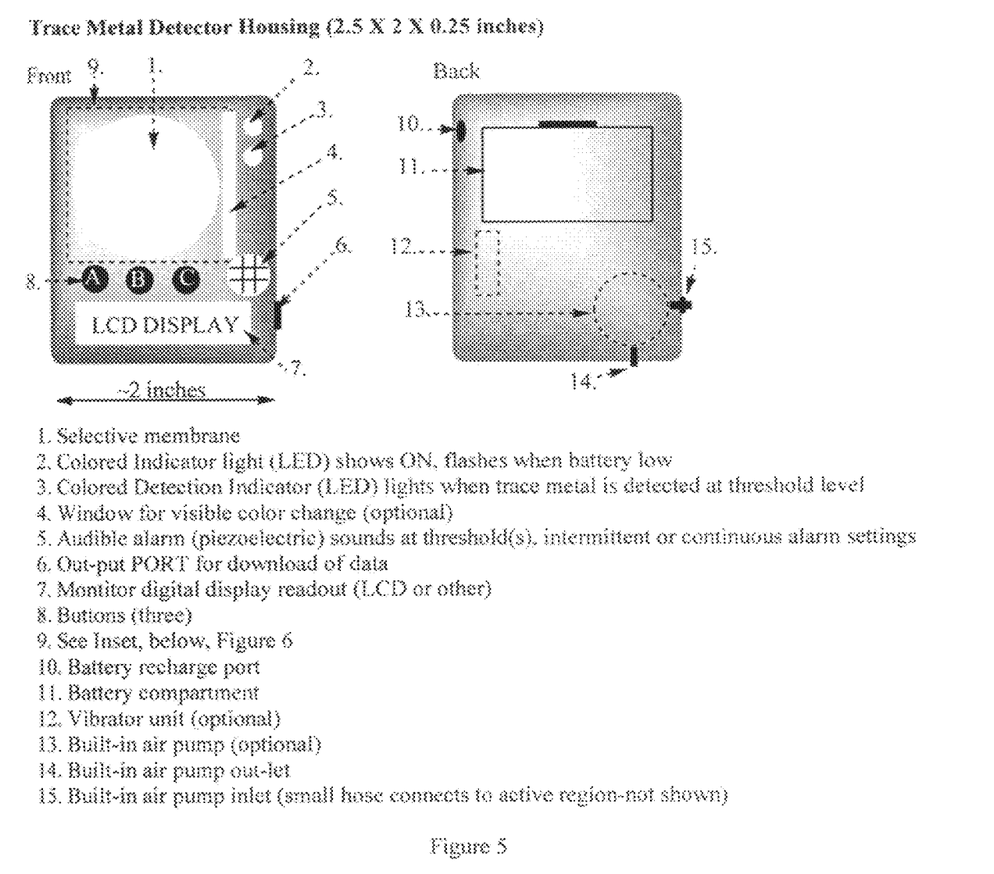
FIG. 5 shows a version of the main components of the detector.
Figure 6:
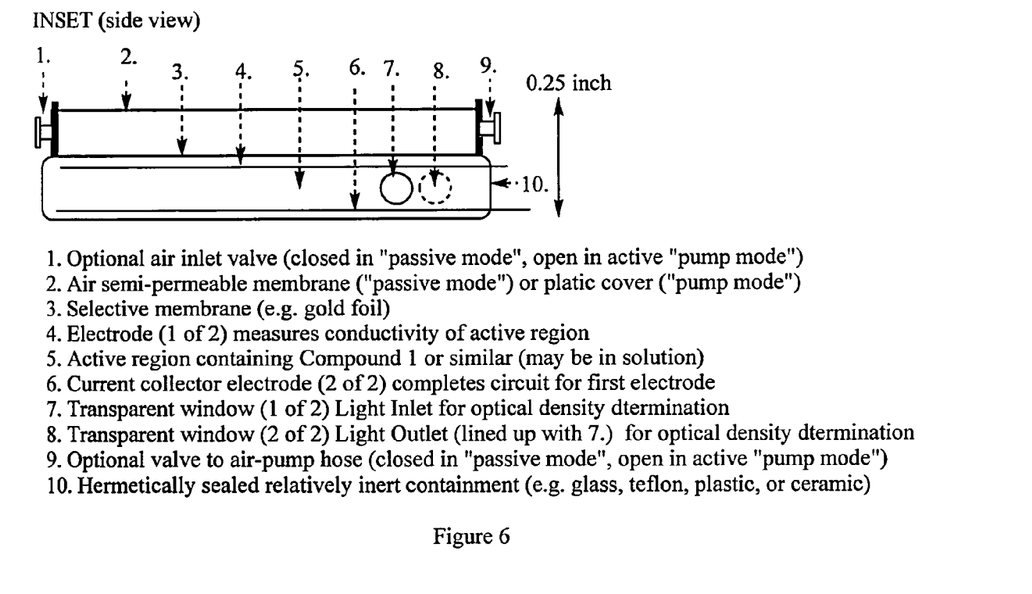
FIG. 6 shows more detail of the cavity region (Inset) of the detector in FIG. 5.

The former spectrophotometric method using the Beer-Lambert Law, which relates the absorbance of light at a specific wavelength to the concentration of a specific analyte in solution, relates the color change to the concentration of mercury or other trace metal via the charge transfer complex formed between the trace metal and the cyclooctatetraene moiety containing compound. The charge transfer complex absorbs light at a very different wavelength than does the neutral electron accepting compound (i.e. Compound 1), yielding a dramatic color change which may be used to quantify the concentration of the element being investigated. Each different charge transfer complex will have a unique wavelength absorbance profile. Thus, different trace metals can be quantified simultaneously by this method by analyzing different absorbance wavelengths. This can be quantified with greater specificity when analyzed by spectrophotometric equipment. Incorporation of a UV-visible light detector could provide for an effective direct read detection and quantitative spectrophotometric analysis. Alternatively, semi-quantitative colorimetric methods can be used to determine the concentration of a trace metal by direct comparison to a color chart of standardized concentrations.

Additionally, the charge transfer complex will have increased conductivity which can be used to quantify the concentration of the relevant element (e.g. mercury). The conductivity form of detection occurs with a change in conductivity in the active media. Such detection could be engineered to be highly sensitive to mercury salts which are formed via electron transfer from mercury to the electron accepting reagent. As more electron accepting reagent is reduced, the conductivity increases.

While the detector detailed herein is primarily intended for use in ambient air, it may also be readily used to detect and quantify the presence of relevant elements in an aqueous environment. In such a case, a known volume of suspected contaminated water is simply placed in direct contact with the selectively permeable membrane. The membrane would permit the relevant element to leach through but preclude the solution (e.g. water) from entering the cavity. As a result the concentration of the relevant element in the solution could be quantitatively measured.

Regardless of the nature of the environment (air, water, or other) where testing occurs, the complexed trace metal (such as mercury) cannot back-flow through the selectively permeable membrane (such as gold foil) once the complex is formed. The trace metal is effectively trapped as a salt complex with the electron accepting reagent confined to the hermetically sealed compartment; the trace metal is effectively sequestered from the environment. Electrochemical and other techniques can be used to reclaim the trace metal and regenerate the active cyclooctatetraene moieties which can then be reused.

The invention claimed is:
1. A trace metal detection substrate comprising:
   a. a solution comprising a molecule, said molecule comprising at least one cyclooctatetraene moiety wherein said cyclooctatetraene moiety is an eight carbon atom cyclic ring wherein said carbon atoms are each covalently bonded to one other atom and wherein said molecule is incorporated into a polymer structure and said cyclooctatetraene moiety remains intact.
2. The trace metal detection substrate of claim 1, wherein said molecule is a monomer of said polymer.
3. A trace metal detection substrate comprising:
   a. a solution comprising a molecule, said molecule comprising at least one cyclooctatetraene moiety wherein said cyclooctatetraene moiety is an eight carbon atom cyclic ring wherein said carbon atoms are each covalently bonded to one other atom and wherein said cyclooctatetraene moiety is annulated by at least one additional cyclic ring and wherein said molecule is incorporated into a polymer structure and said cyclooctatetraene moiety remains intact.
4. The trace metal detection substrate of claim 3, wherein said molecule is a monomer of said polymer.
5. The trace metal detection substrate of claim 3, wherein said molecule comprises at least two cyclooctatetraene moieties.
6. The trace metal detection substrate of claim 5, wherein said molecule is a monomer of said polymer.
7. A trace metal detection badge comprising:
   a. a cavity cell;
   b. separated from the environment via a hermetically sealed enclosure and at least one selectively permeable membrane; and
   c. said cavity containing a solution comprising a molecule, said molecule comprising at least one cyclooctatetraene moiety wherein said cyclooctatetraene moiety is an eight carbon atom cyclic ring wherein said carbon atoms are each covalently bonded to one other atom wherein said other atoms are a proton, deuterium, carbon, or a halogen.
8. The trace metal detection badge of claim 7, wherein said enclosure comprises at least one electrode extending into the cavity cell.
9. The trace metal detection badge of claim 7, wherein said enclosure comprises at least one transparent section.
10. The trace metal detection badge of claim 7, wherein said enclosure comprises at least one light emitting diode.
11. The trace metal detection badge of claim 7, wherein said enclosure comprises at least one digital display.
12. The trace metal detection badge of claim 7, wherein said enclosure comprises at least one speaker.
13. The trace metal detection badge of claim 7, wherein said enclosure comprises at least one control button.
14. The trace metal detection badge of claim 7, wherein said trace metal detection badge comprises at least one computer chip for storage of electronic data.
15. The trace metal detection badge of claim 14, wherein said enclosure comprises at least one access port for the downloading of electronic data.
16. The trace metal detection badge of claim 7, wherein said enclosure is intrinsically safe.
17. The trace metal detection badge of claim 7, wherein said enclosure comprises an oscillator capable of producing vibrations.

* * * * *